United States Patent
Schnell et al.

(12)

(10) Patent No.: US 6,630,321 B1
(45) Date of Patent: Oct. 7, 2003

(54) METHOD FOR IDENTIFYING A COMPOUND THAT MODULATES THE FUNCTION OF THE GENE PRODUCT OF AN ESSENTIAL GENE

(75) Inventors: Norbert Friedeman Schnell, Aalen (DE); Jini Suberna Chavda, Macclesfield (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/980,686

(22) PCT Filed: Jun. 27, 2000

(86) PCT No.: PCT/GB00/02472
§ 371 (c)(1),
(2), (4) Date: Dec. 7, 2001

(87) PCT Pub. No.: WO01/02605
PCT Pub. Date: Jan. 11, 2001

(30) Foreign Application Priority Data

Jul. 2, 1999 (GB) .............................................. 9915399

(51) Int. Cl.⁷ .............................. C12Q 1/00; C12Q 1/02
(52) U.S. Cl. .................................. 435/29; 435/4; 435/6
(58) Field of Search .................................. 435/4, 6, 29

(56) References Cited

U.S. PATENT DOCUMENTS 5,527,687 A * 6/1996 Kirsch et al. .................. 435/14

FOREIGN PATENT DOCUMENTS

| EP | 0 626 453 A | 11/1994 |
| EP | 0 972 847 A2/3 | 1/2000 |
| WO | WO 96/23075 | * 8/1996 |
| WO | WO 96/40979 | * 12/1996 |
| WO | WO 99 31269 A | 6/1999 |

* cited by examiner

Primary Examiner—James Ketter
Assistant Examiner—Daniel Sullivan
(74) Attorney, Agent, or Firm—Fish & Richardson P.C.

(57) ABSTRACT

A method for identifying a compound which modulates the function of the gene product of an essential gene, which method comprises providing viable cells wherein the gene is expressed under the control of a heterogenous, regulatable promoter, switching off gene expression via the promoter, contacting the cells with a test compound and determining any modulatory effect of the compound on the function of the gene product.

25 Claims, 5 Drawing Sheets

Legend Fig2):
The culture is shifted from galactose to glucose at time 0, whereby new synthesis of Erg11p (lanasterol C-14-demethylase) is stopped.
The fluconazole concentration is sub-inhibitory (e.g. 10 mg/l) for a wild type (wt) strain.

——————————— : no fluconazole
- - - - - - - - - - - - - : fluconazole threshold: Erg11p activity is now rate-limiting for growth.

METHOD FOR IDENTIFYING A COMPOUND THAT MODULATES THE FUNCTION OF THE GENE PRODUCT OF AN ESSENTIAL GENE

This application is the National Phase of International Application PCT/GB00/02472 filed Jun. 27, 2000 which designated the U.S. and that International Application was published under PCT Article 21(2) in English.

This invention provides methods for the identification of novel biological targets and/or inhibitors. Such methods provide useful and convenient tools for high throughput screening. In particular, such methods may be used to identify novel antimicrobial agents.

The emergence of resistance to current therapeutic agents, such as antibacterial, antifungal, and antimalarial agents, necessitates the development of novel agents. Whilst target-based biochemical screens can be successful, classic anti-microbial screening has clearly outperformed rational target-selecting procedures in terms of discovered novel antimicrobials. Target-based biochemical screens are frequently seen to invoke a lack of cell activity, despite a good inhibition of the target enzyme, perhaps due to low permeation into or export out of the cell. Also the presence of inhibiting structures for a hand-picked target within a limited set of available molecules is by no way guaranteed.

In contrast, cell-based antimicrobial screening frequently identifies antimicrobial action but then either reveals this inhibition to be caused by general toxicity, for example membrane perturbation or DNA-intercalation, or fails to identify any specific interaction of the drug with the cellular machinery. This complicates chemical optimisation of initial leads, providing no guide for a structure-activity relationship.

A particular approach to identify target-based mode of action has been that of hypersensitivity.

Historically, the way to generate hypersensitive versions of a protein of interest has been the generation of temperature-sensitive (ts) mutations in its encoding gene (Schmid et al. Genetics 123, pp625–633, (1989)). Temperature sensitive (Ts) or other conditional phenotypes can be generated by either targeted (for example using PCR) or random (for example using chemicals or radiation) mutagenesis. However, such conditional mutants are frequently hypersensitive to inhibitors even under permissive conditions.

We have now found that hypersensitivity to inhibitors can be readily achieved by shutting down a particular essential function of viable cells followed by analysis of the effects in the presence/absence of a potential inhibitor. By "shutting down" we mean that the particular essential function is not available to the cells at any expression level.

Therefore in a first aspect of the present invention we provide a method for identifying a compound which modulates the function of the gene product of an essential gene, which method comprises providing viable cells wherein the gene is expressed under the control of a heterogeneous, regulatable promoter, switching off gene expression via the promoter, contacting the cells with a test compound and determining any modulatory effect on the function of the gene product.

The method provides a step jump in the feasibility of a complete genome analysis for compound hypersensitivity. It provides a number of significant advantages not least that the unaltered "normal" protein is used in contrast to for example extrapolation from the interaction of an altered, mutagenized protein with an inhibitor onto the interaction of the same chemical. Also no effort is needed to fine tune promoter activity to a higher or lower level. Inhibition of one specific biochemical entity, for example a protein required for cellular growth or survival is conveniently indicated by a hypersensitive response of the strain with the regulatable gene compared to its unaltered parent.

By "heterogeneous, regulatable promoter" we mean a promoter other than the native promoter for the essential gene and which can be regulated by the addition and/or removal of specific materials or for example by other environmental changes.

By "hypersensitivity" we mean a larger reduction in cell growth in the presence of an identical concentration of drug, compared to a wild-type cell.

Furthermore, hypersensitivity caused by underexpression of one specific enzyme can extend to a whole biochemical pathway, such as for example sterol biosynthesis. This is exemplified by the results shown in FIG. 5 of this invention, where the sensitivity to terbinafine is altered both by shutdown of the target enzyme (encoded by ERG1) as well as shutdown of another enzyme (encoded by ERG11) in the same pathway.

By "viable" we mean cells that have grown sufficiently so that when gene expression of an essential gene is turned off, meaningful measurements and kinetic analysis may be made. The cells are preferably allowed to grow into early stationary phase by which time a final optical density reading is taken. A reduced optical density compared to no drug or no switchoff controls is interpreted as growth inhibition.

By "essential gene" we mean a gene required by a cell for example for cell growth and/or cell viability. This does include genes required only under certain assayable conditions (ie conditional essential). In its simplest manifestation essentiality is defined as necessary for growth of the organism on rich media (For a comprehensive summary of such media as well as general yeast methodology see Sherman et al in Methods in Enzymology, Vol 194, Guthrie and Fink eds, Academic Press (1991). Convenient genes include fungal and bacterial genes.

By "switching off gene expression" we mean that all gene expression is turned from ON to OFF. There is no low level gene expression in the OFF position.

By "cells" we mean cells from any convenient source, these include human, animal or microbial cells. New genome-based techniques are developing which combine screening of compounds with simultaneous target identification. Whilst this invention is of particular use with genetically tractable model organisms such as Schizosaccharomyces pombe and Saccharomyces cerevisiae, it is universally applicable and is limited only by practical considerations. Using model organisms such as *S. cerevisiae, S. pombe, C. elegans,* or *D. melanogaster* it is possible to study conserved functions of eukaryotes. The application of genetics using human or animal cell lines directly, then extends possibilities further.

Any convenient test compound such as a peptide, nucleic acid and low molecular weight compound, may be used in the methods of the invention. Preferred test compounds are potential therapeutic agents or may be used in further studies to identify therapeutic agents. Particular test compounds are low molecular weight compounds of, for example, molecular weight of less than 1000, such as less than molecular weight 600.

The modulatory effect of a compound on the gene product of an essential gene is conveniently investigated taking endpoint optical density readings (the higher the absolute optical density of the culture, the less inhibition is thought to have occured. Such analysis is conveniently effected over period of typically 24 hours for yeast cells. Bacteria may take significantly shorter (eg 12 hours) whereas higher eukaryotic cells will require several days to reach early stationary growth phase. The analysis is conveniently photometric (optical density of the culture at 600 nm wavelength).

Importantly, the combination of very recent techniques for site specific integration of DNA (for example with a switchable promoter directly replacing the native one) with the observed fixed timepoint optical density analysis of the hypersensitive response (as further elaborated below) is novel and allows exploitation for large-scale drug screening, compound and target profiling. Moreover, such strains are also very easily obtainable in very high quantity (ie. thousands of genes in S. cerevisiae).

Some examples of switchable promoters for use in S. cerevisiae include MET3 (repressible by added methionine) and GAL1 (repressed by glucose induced by galactose); for use in S. pombe: NMT1 (repressed by thiamine); for use in C. albicans: MAL1 (repressed by glucose, induced by maltose, sucrose); for use in E. coli: araB (repressed by glucose, induced by arabinose); for use in Gram-positive bacteria such as Staphylococci, Enterococci, Streptococci and Bacilli: xylA/xylR (from S. xylosus) (repressed by glucose, induced by xylose); for use in E.coli and B.subtilis pSPAC (an artificial promoter derived from E.coli lac, regulated by IPTG, see Vagner et al. Microbiology (1998), 144, 3097–3104); and for all of the above organisms plus further unspecified fungi, bacteria and mammalian cell lines: tetA/tetR (from various bacterial tetracycline resistance cassettes) this system exists in various versions, see Gossen et al. Current Opin. Biotechnol. 5, pp516–520 (1994), that are repressible or inducible by various tetracycline analogues.

We illustrate in the Example and Figures below that it is possible to generate hypersensitivity towards any agent that inhibits a biochemical function by placing the gene encoding that function (protein or RNA) under control of a tightly regulatable promoter and switching it from the ON to the OFF state whilst simultaneously adding the interacting substance (for illustration of such a switch see FIG. 1). Whilst it is known to place external promoters in front of genes of interest to achieve over- or under-expression of the encoded protein, this process requires labour-intensive fine-tuning and setting up. Due to strongly varying expression levels, every gene of interest would require a different tuning of its promoter strength to be at a just growth-rate-limiting level. Therefore such a protocol relying on fine-tuning is unlikely to allow implementation at the high throughput scale necessary for genomic analysis.

Our novel findings, as detailed in the experiments shown below, demonstrate that a simple and standard protocol using just one promoter at clearly defined ON and OFF states (ie. explicitly without any finer modulation of the expression level) is capable to generate accurate measurements of specific hypersensitivity due to target underexpression. The underexpression is caused by i) decay of the RNA, ii) decay of the target protein, iii) dilution of the target molecule into several daughter cells during cell growth in the absence of any resynthesis.

The examples below demonstrate, for example, that unknown fungal target proteins that can be inhibited by compounds can be identified by placing their essential genes under control of a regulatable promoter, switching it off and exposing it to compound levels that do not inhibit the corresponding wild type cell. Currently 814 S. cerevisiae genes have been shown essential for growth even on rich media, (source YPD™.) An observed hypersensitive response (eg in a fungus such as S. cerevisiae) shows: i) the target is essential ii) the compound is an antifungal agent or a starting point for evolution of a more potent analogue iii) the matching target-compound pair (or pairs) establishes mode of action for the antifungal compound. For more than one compound detected against one target, valuable structure-activity relationship (SAR) information can be obtained. Comparison and pattern recognition analysis of many compound effects on many targets will establish a valuable database useful for grouping novel targets into pathways immediately. Hypersensitivity also allows the target-specific detection of low potency compounds not identifiable using the parental strain.

A further advantage of the invention is that characterised biochemical activity of the target molecule is not a prerequisite for the methods of the invention. Hypersensitivity as such can provide an assayable feature intrinsically linked with a specific target. Genomic switchoff constructs can be generated and integrated into the organisms genome in very high throughput using published PCR-based methodology without the involvement of any cloning step (Longtine et al. Yeast, 14, pp 953–961 (1998); Zhang et al. Nature Genetics, 20, pp 123–128 (1998). Therefore the methods of the invention may be used to test as many compounds as possible against every potential antifungal target, for example up to 10, up to 20, up to 50, up to 100, up to 500, or up to 1000 targets using modern high throughput screening technology.

Therefore in a further method of the invention we provide a method for identifying metabolic pathway drug hypersensitivity which method comprises providing viable cells wherein a gene in the metabolic pathway is expressed under the control of a heterogenous, regulatable promoter, switching off expression of the gene via the promoter, contacting different groups of the cells with different test compounds, determining and comparing any modulatory effect on the growth of the viable cells. Underexpression of one element of a biochemical pathway and chemical inhibition of another part has been shown to be synergistic (see FIG. 5) thus generating pathway specific information by underexpressing just one element of that pathway.

The invention will now be illustrated but not limited by reference to the following Example and Figures wherein:

FIG. 1 shows the generation of a controllable allele of gene, Gen1, by replacing its native promoter with a well defined and tight ON/OFF switch; here GAL1

FIG. 2 shows Erg11p activity in wild type (wt) and GAL1-ERG11 strains and illustrates how catalytic activity declines both with time and increased concentration of an inhibitor. The culture is shifted from galactose to glucose at time 0, whereby new synthesis of Erg11p (lanosterol C-14-demethylase) is stopped. The fluconazole concentration is sub-inhibitory (for example 10 mg/l) for a wild type (wt) strain.; ___.no fluconazole, . . . : fluconazole; the threshold is where Erg11p activity is rate-limiting for growth.

FIG. 3 shows the growth of wild type (JK9-3da, Kunz et al. Cell, 73, pp585–596(1993)), GAL1-ERG11 and GAL1-AUR1 (generated as described in Longtine et al. Yeast, 14, pp 953–961 (1998))strains in the presence of fluconazole;

EXAMPLE

Figure 1:
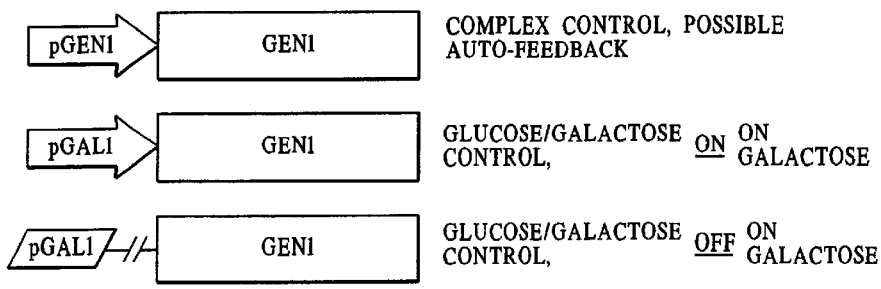
Figure 2:
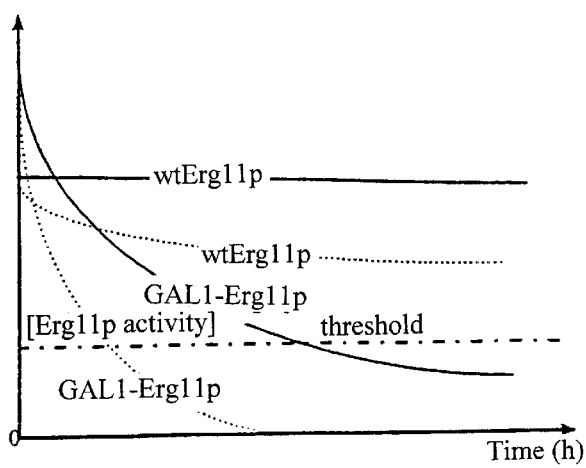

The Ergosterol and Sphingolipid Biosynthetic Pathways of *S. cerevisiae*: a Study With Known Inhibitors The rationale in using a complete switchoff instead of a low expressor is detailed as follows exemplified for Erg11p (p=protein), the lanosterol C-14-demethylase, a fungal enzyme in the ergosterol biosynthetic pathway: The drug fluconazole, like other azole antifungals, inhibits Erg11p leading to a decreased total activity within the cell. However no reduction in growth will be observed as long as the amount of active Erg11p is high enough not to be rate limiting for growth (above the threshold, see FIG. 2) In our example the fluconazole concentration is insufficient to reduce Erg11p activity below this threshold. The situation for a GAL1-driven ERG11 gene is different however: At time 0 the gene's engineered promoter is switched from the ON state (because of the high expression of a GAL1 promoter this level is usually higher than for the native promoter) to the OFF state by changing the carbon source in the culture. From this timepoint on no new mRNA is transcribed and—after decay of the mRNA—no new Erg11 protein is being synthesized. Erg11 concentrations are now falling due to the dilution of the enzyme into new daughter cells and protein decay of Erg11p. As soon as the threshold line is crossed (FIG. 2) Erg11p becomes rate-limiting ie the strain shows a reduced growth rate compared to the unaltered parental strain (wt). This is reflected by a lower final optical density of the culture. The presence of the inhibitor fluconazole titrates active Erg11p molecules rendering them inactive. Therefore the threshold-line is crossed earlier, as no new Erg11p can be synthesized. Compared to the wild-type cell, this is seen as hypersensitivity (larger reduction in growth in the presence of an identical concentration of drug). Simplified one can explain this as a reduced amount of cell-doublings before rate-limiting conditions occur.

Figure 3:
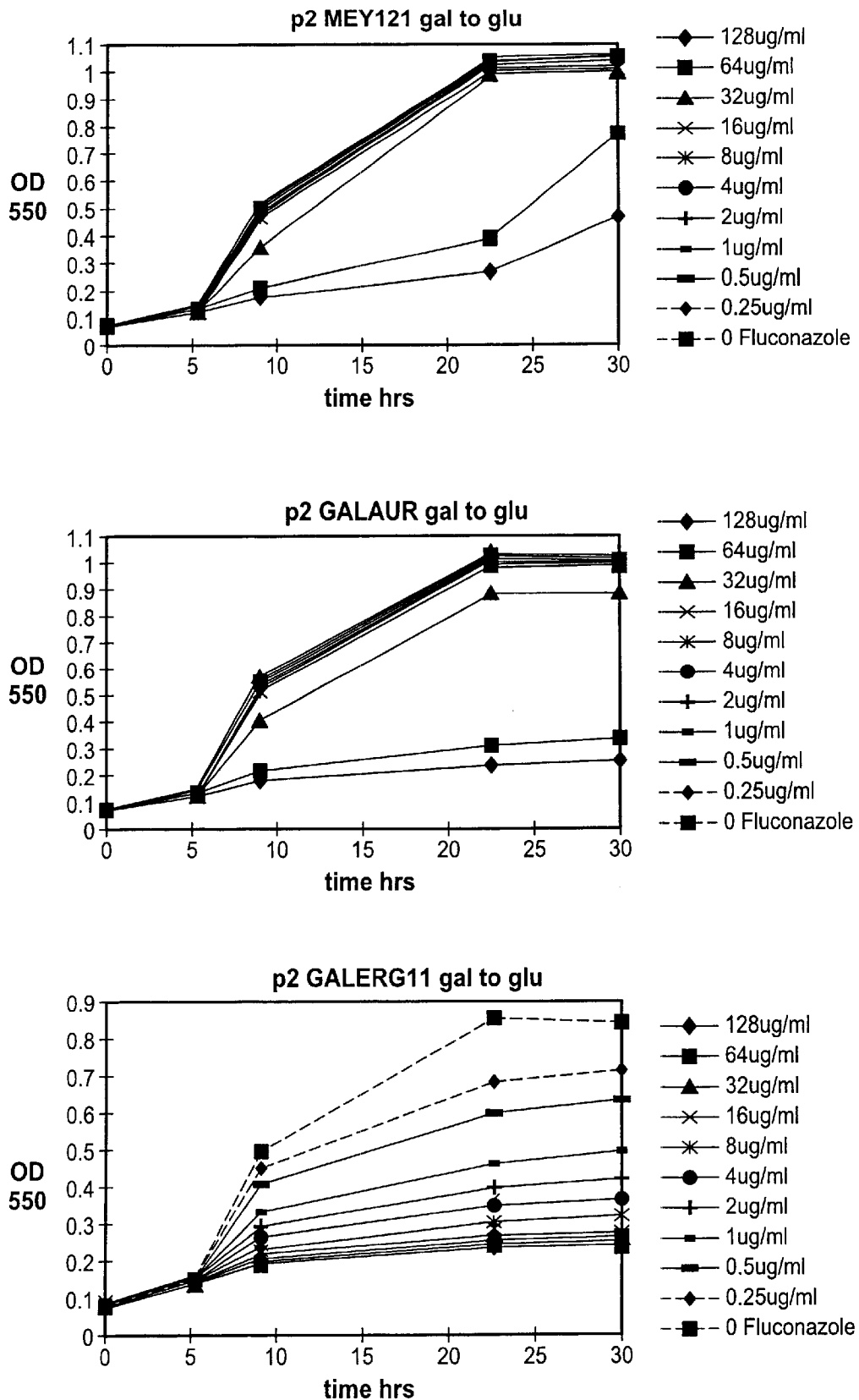
Figure 4:
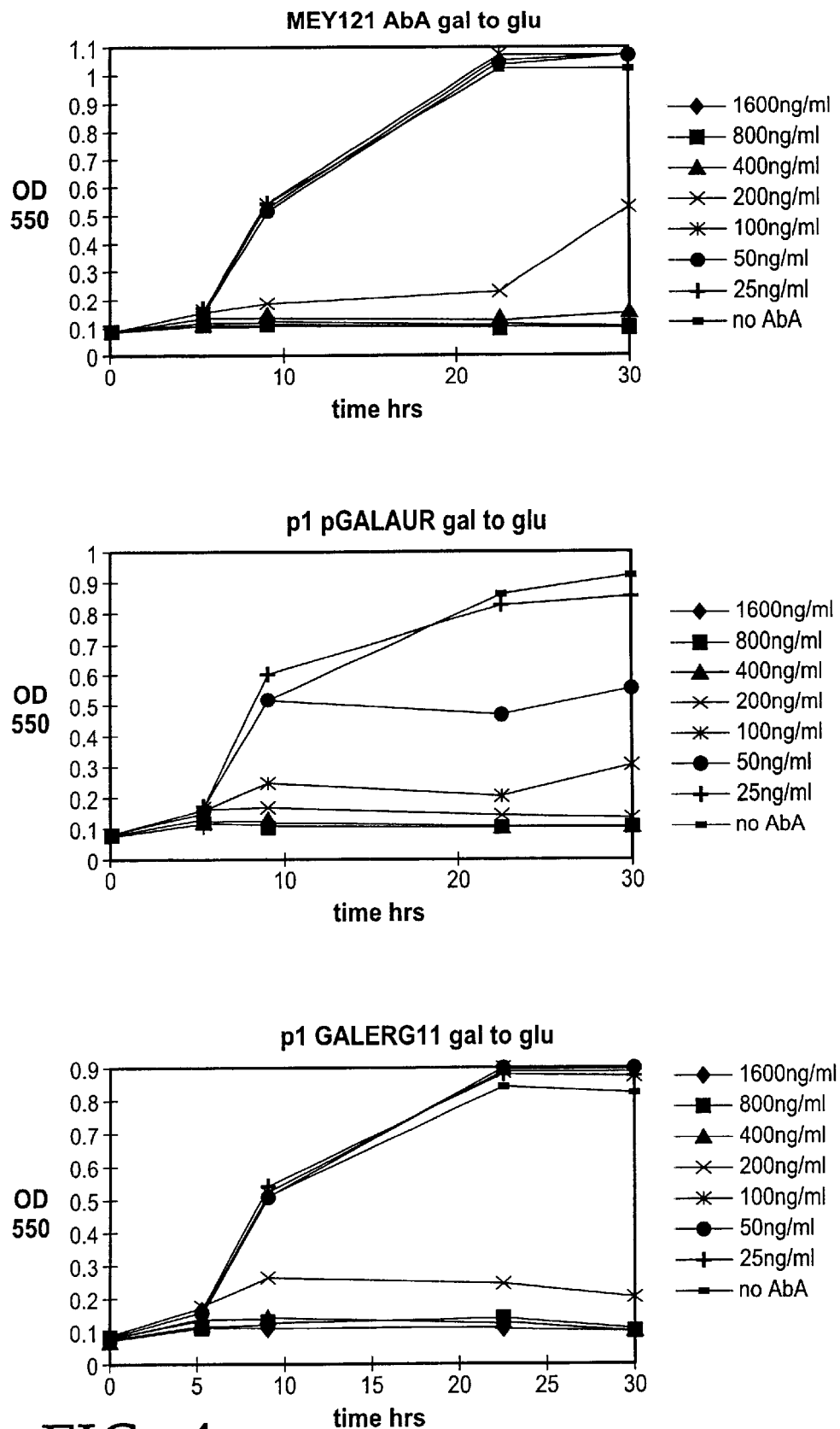
FIG. 4 shows the growth of wt, GAL1-ERG11, and GAL1-AUR1 strains in the presence of aureobasidinA.

For target and compound evaluation the hypersensitivity has to be specific for certain drug-target combinations. Therfore the method was tested and validated with another unrelated known drug-target combination: The AUR1 gene encodes inositolphosphorylceramide (IPC) synthase, an essential enzyme of the fungal sphingolipid biosynthetic pathway (Nagiec et al, J.Biol.Chem., 1997, 272,15, 9809–9817). The enzyme is inhibited by the natural product aureobasidinA with sub nanomolar potency, leading to an antifungal action of the drug. Like ERG11, AUR1 was subjected to a promoter swap and the resulting yeast strains were the parent (wt), GAL1-ERG11 and GAL1-AUR1. They were tested for their sensitivity towards both drugs, fluconazole and aureobasidinA. As predicted by our theory both GAL1-driven strains showed a prominent hypersensitive response towards their cognate drugs (see FIGS. 3 and 4). Remarkably, there was no cross reaction ie GAL1-ERG11 showed no increased sensitivity towards aureobasidinA, neither did GAL1-AUR1 show hypersensitivity to fluconazole. This result confirms our theory and proves applicability and utility of the described method as a drug and target discovery tool.

Figure 5:
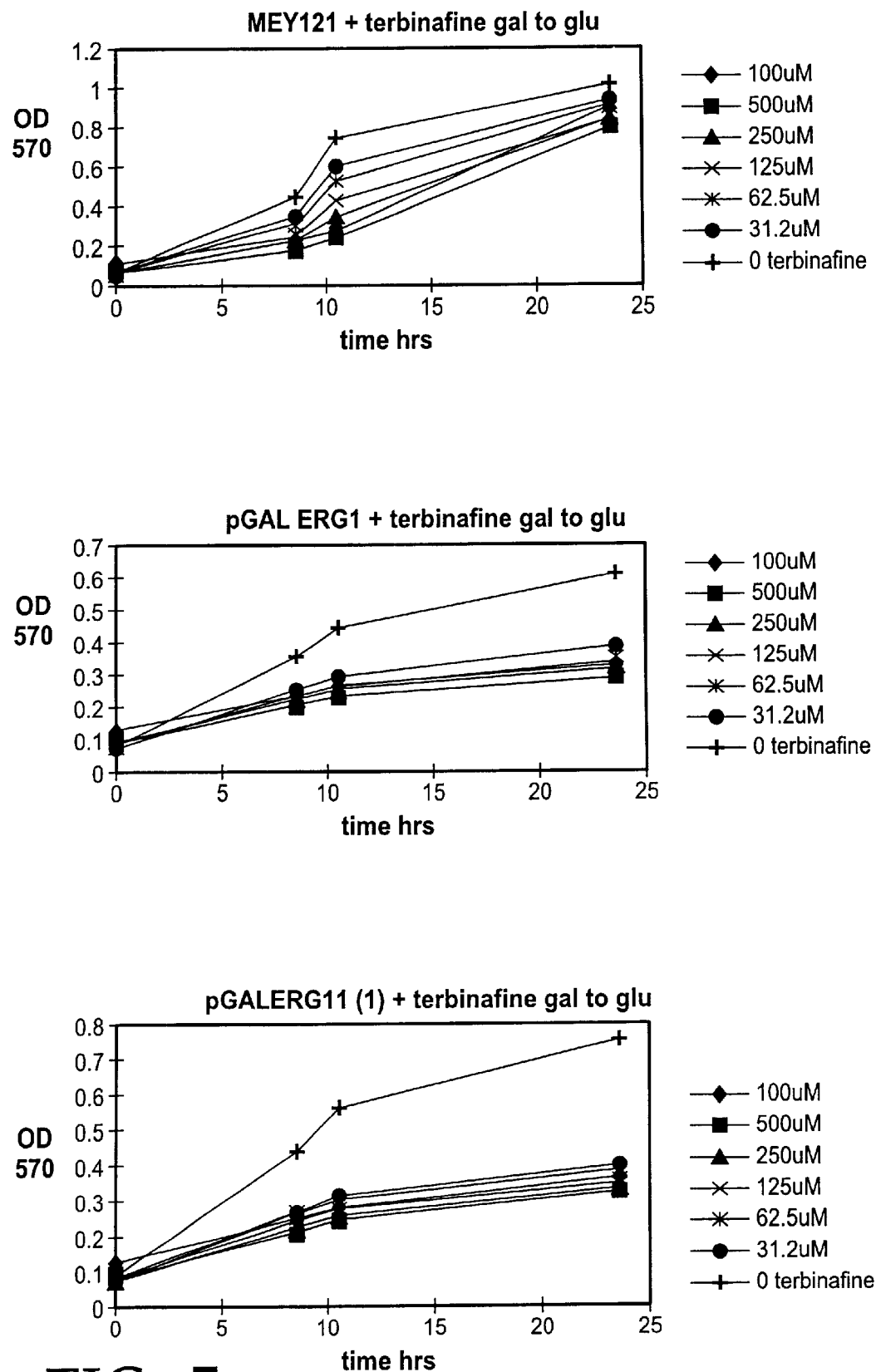
FIG. 5 shows the growth of wt, GAL1-ERG11, and GAL1-AUR1 strains in the presence of terbinafine.
Figure 6:
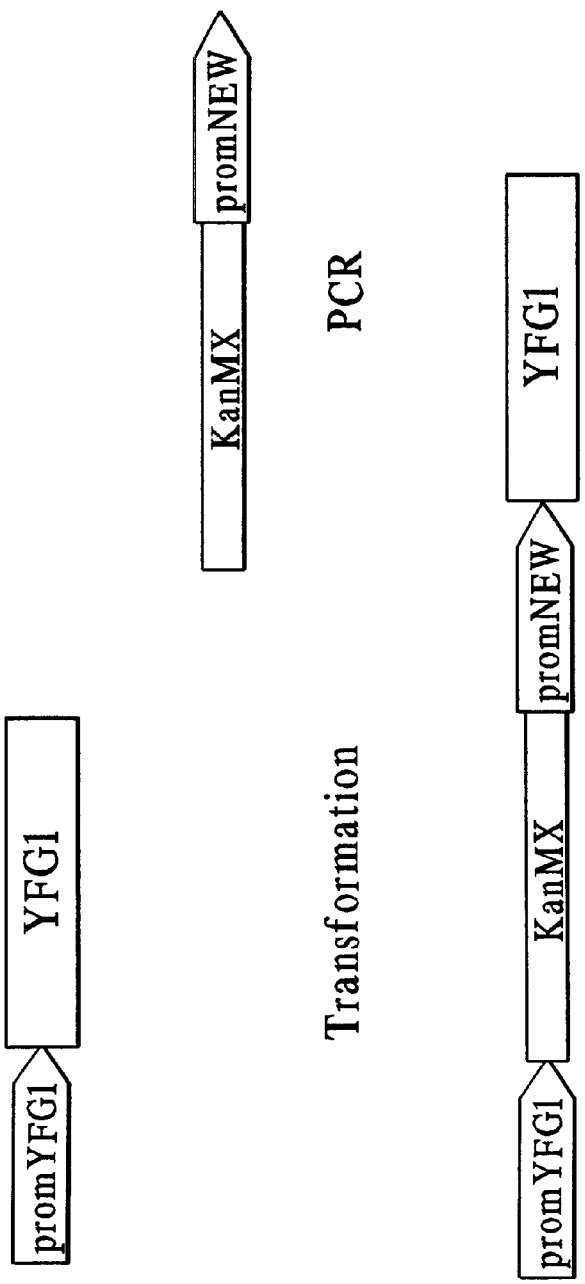
FIG. 6 shows a protocol for promoter replacement in S. cerevisiae (substantially as described in Longtine et al. Yeast, 14, pp 953–961 (1998)).

It follows that the hypersensitive reaction towards an inhibitor of one enzyme in a pathway may be extended to inhibitors of the whole pathway. This is due to the linear arrangement of enzymes in a biochemical cascade of reactions where one enzyme provides substrate for the next. A reduced substrate supply can act synergistically with a reduced enzyme level. Thus the activity of the almost rate-limiting enzyme Erg11p (after switchoff) will be reduced further by withdrawal of its substrate normally provided by Erg1p, squalene epoxidase, another enzyme of the sterol biosynthetic pathway, through several biochemical steps. Erg1p is now inhibited by terbinafine. Any such pathway specific hypersensitivity allows the categorisation of (uncategorised) genes into the same pathway as the switched off gene. To investigate this, we examined Erg1p. This enzyme has been shown to be inhibited by the antifungal terbinafine but Erg11p is not. As shown in FIG. 5, GAL1-ERG11 is as hypersuscepible to terbinafine as GAL1-ERG1, proving the postulated cross-pathway hypersensitivity. This pathway-specific analysis tool will be extremely useful for the classification of novel inhibitors (with unknown mode of action).

It will be appreciated that whilst exemplified particularly for *S. cerevisiae*, this invention is universally applicable in all genetically manipulatable organisms such as bacteria.

What is claimed is:

1. A method for identifying a compound which modulates the function of the gene product of a gene essential for cell growth and/or cell viability under assayable conditions, which method comprises:
    (a) providing viable cells wherein the gene is expressed under the control of a heterogenous, regulatable promoter;
    (b) switching off expression via the promoter;
    (c) contacting the cells with a test compound; and
    (d) determining a modulatory effect on the function of the gene product.

2. A method as claimed in claim 1, wherein the viable cells in step (a) have grown into early stationary phase.

3. A method as claimed in claim 1, wherein the gene is a bacterial gene.

4. A method as claimed in claim 1, wherein the gene is a fungal gene.

5. A method as claimed in claim 1, wherein the modulatory effect is determined via optical density measurements.

6. A drug screening method which comprises using a method as claimed in claim 1 to test a plurality of test compounds against gene products of more than one essential gene.

7. A method as claimed in claim 6, wherein the compounds are tested against the gene products of more than 20 essential genes.

8. A method for identifying metabolic pathway drug hypersensitivity, which method comprises:
    providing viable cells wherein a gene in the metabolic pathway is expressed under the control of a heterogenous, regulatable promoter;
    switching off expression of the gene via the promoter;
    contacting a first population of the cells with a first test compound;
    contacting a second population of the cells with a second test compound different from the first test compound; and
    determining and comparing a modulatory effect of the first and second test compounds on the growth of the cells.

9. A method as claimed in claim 2, wherein the gene is a bacterial gene.

10. A method as claimed in claim 2, wherein the gene is a fungal gene.

11. A method as claimed in claim 5, wherein the viable cells in step (a) have grown into early stationary phase.

12. A method as claimed in claim 5, wherein the gene is a bacterial gene.

13. A method as claimed in claim 5, wherein the gene is a fungal gene.

14. A method as claimed in claim 6, wherein the viable cells in step (a) have grown into early stationary phase.

15. A method as claimed in claim 6, wherein the gene is a bacterial gene.

16. A method as claimed in claim 6, wherein the gene is a fungal gene.

17. A method as claimed in claim 6, wherein the modulatory effect is determined via optical density measurements.

18. A method as claimed in claim 7, wherein the viable cells in step (a) have grown into early stationary phase.

19. A method as claimed in claim 7, wherein the gene is a bacterial gene.

20. A method as claimed in claim 7, wherein the gene is a fungal gene.

21. A method as claimed in claim 7, wherein the modulatory effect is determined via optical density measurements.

22. A method as claimed in claim 8, wherein the viable cells have grown into early stationary phase.

23. A method as claimed in claim 8, wherein the gene is a bacterial gene.

24. A method as claimed in claim 8, wherein the gene is a fungal gene.

25. A method as claimed in claim 8, wherein the modulatory effect is determined via optical density measurements.

* * * * *

UNITED STATES PATENT AND TRADEMARK OFFICE
CERTIFICATE OF CORRECTION

PATENT NO. : 6,630,321 B1
DATED : October 7, 2003
INVENTOR(S) : Norbert Friedemann Schnell and Jini Suberna Chavda It is certified that error appears in the above-identified patent and that said Letters Patent is hereby corrected as shown below:

<u>Title page,</u>
Item [75], Inventors, replace with the following:
-- Norbert Friedemann Schnell, Aalen
 (DE); Jini Suberna Chavda,
 Macclesfield (GB) --.

Signed and Sealed this

Eleventh Day of October, 2005

JON W. DUDAS
*Director of the United States Patent and Trademark Office*